United States Patent
Cereda et al.

(10) Patent No.: US 7,164,018 B2
(45) Date of Patent: Jan. 16, 2007

(54) POLYMERS BASED ON N-CARBAMYL-N'-DIMETHYLSILYL METHYL-PIPERAZINE TRACELESS LINKERS FOR THE SOLID PHASE SYNTHESIS OF PHENYL BASED LIBRARIES

(75) Inventors: Enzo Cereda, Novi Ligure (IT); Carlo Maria Pellegrini, Casalpusteriengo (IT); Monica Quai, Milan (IT); Walter Barbaglia, Milan (IT)

(73) Assignee: Boehringer Ingelheim International GmbH, Ingelheim (DE)

( * ) Notice: Subject to any disclaimer, the term of this patent is extended or adjusted under 35 U.S.C. 154(b) by 533 days.

(21) Appl. No.: 10/766,981

(22) Filed: Jan. 29, 2004

(65) Prior Publication Data

US 2004/0186243 A1    Sep. 23, 2004

Related U.S. Application Data

(62) Division of application No. 10/058,433, filed on Jan. 28, 2002, now Pat. No. 6,740,712.

(60) Provisional application No. 60/273,312, filed on Mar. 2, 2001.

(30) Foreign Application Priority Data

Jan. 29, 2001   (EP)   ................... 01101946

(51) Int. Cl.
  *C07F 7/10*   (2006.01)
(52) U.S. Cl. ...................... 544/229
(58) Field of Classification Search ............... 544/229
   See application file for complete search history.

(56) References Cited

U.S. PATENT DOCUMENTS

| | | | |
|---|---|---|---|
| 4,202,356 A | 5/1980 | Digenis et al. |
| 4,883,608 A | 11/1989 | Trujillo et al. |
| 6,126,867 A | 10/2000 | Kanitz et al. |
| 6,127,489 A | 10/2000 | Newlander |
| 6,147,159 A | 11/2000 | Hu et al. |
| 6,433,100 B1 | 8/2002 | Kramer et al. |

FOREIGN PATENT DOCUMENTS

EP     472304    *   2/1992

* cited by examiner

*Primary Examiner*—Bernard Lipman
(74) *Attorney, Agent, or Firm*—Michael Morris; Mary-Ellen M. Devlin; Thomas Blankinship

(57) ABSTRACT

The present invention relates to polymers characterized by novel silicon linkers based on the carbamyl piperazine moiety, methods of preparing these polymers and their use in the solid phase synthesis of compounds or libraries of compounds embracing a phenyl ring in their structure.

2 Claims, No Drawings

POLYMERS BASED ON N-CARBAMYL-N'-DIMETHYLSILYL METHYL-PIPERAZINE TRACELESS LINKERS FOR THE SOLID PHASE SYNTHESIS OF PHENYL BASED LIBRARIES

This is a divisional of prior application U.S. Ser. No. 10/058,433, filed on Jan. 28, 2002, now U.S. Pat. No. 6,740,712, and which claims benefit of U.S. Provisional Application Ser. No. 60/273,312, filed on Mar. 2, 2001, both of which applications are incorporated herein in their entirety.

The present invention relates to polymers characterised by novel silicon linkers based on the carbamyl piperazine moiety, methods of preparing these polymers and their use in the solid phase synthesis of compounds or libraries of compounds embracing a phenyl ring in their structure. Owing to the peculiar chemistry of the silicon atom, when breaking this linkage, an hydrogen atom (or other different groups) substitutes the silicon itself. Therefore the released compounds show no trace of the tethering point (in the hydrogen case) or show further diversity (when additional groups are inserted).

BACKGROUND OF THE INVENTION

Solid phase organic chemistry (SPOC) which was originally developed for peptide and oligo nucleotide synthesis, is now widely applied as an organic synthesis tool in the preparation of small molecules. The SPOC methods are exploited both by academic and pharmaceutical researchers to produce compounds, in limited number or as part of large libraries, to be submitted to high throughput screening in the search for new leads to address the increasing number of therapeutic targets.

The advantages of SPOC over the solution approach are well recognised (reactions driven to completion by excess reagent, easy purification by filtration and easy automation of the processes) and the limitations as well (not all the reactions are amenable to solid phase, e.g. hydrogenation, traditional analytical methods poorly amenable for in process control, continuous need of developing new synthetic methods).

In addition to the attach-detach steps which need chemistry development, the chemical groups involved both in the linkage and in the spacers sometime pose limitation to the chemistries to be carried out to assemble the desired compound and consequently deserve special attention. In former times the attachment relied on traditional hydrophilic groups such as hydroxy, amine and carboxy taking advantage of the knowledge coming from the protective groups chemistry.

Such handles have clear drawbacks as they are stable only under limited conditions and as a common feature, upon detaching they leave the precursor groups on the final molecule as a trace of the attachment point. Moreover when the anchoring point is on a phenyl ring, the presence of hydroxyl, carboxyl or amino groups may be detrimental from the biological point of view. In many cases these groups negatively affect the interaction with the receptor sites and are responsible for low absorption and fast metabolism when compounds of pharmacological interest are tested in vivo. If considering that a phenyl ring is present at least in 70% of compounds endowed with biological activity it is worthwhile developing methods which allow a phenyl ring to be used as an attachment point and in the same time the released compounds don't show any trace of the anchoring point, unless other groups are desired to expand diversity.

DETAILED DESCRIPTION OF THE INVENTION

The most widely exploited class of traceless linkers are those based on the silicon chemistry. These lead to a phenyl ring with no trace of the anchoring point owing to an ipso-desilylation process under acidic conditions (TFA) or to a fluoride mediated cleavage under basic conditions [tetrabuthyl ammonium fluoride (TBAF)]. According to a further option other non polar functionalities such as nitro, bromo or acetyl can be introduced, if desired, during the detachment step.

Now here we describe and this is the object of the present invention, a new linker based on the silicon chemistry as far as the phenyl anchoring point is concerned but exploiting an alternative and advantageous linkage on the resin. The handle or linker is built around a piperazine moiety: one nitrogen connects the silicon containing chain to the target phenyl ring whereas the second one serves to tether the whole structure to the resin. This anchorage relies on a urea type linkage and it is simply obtained by reacting the free piperazine nitrogen with a Merrifield isocyanate resin. This very simple process allows an high yield coupling step avoiding an excess of the precious reagent and an easy in process control (e.g. by following the disappearance of the isocyanate signal and the formation of the urea bond by FT_IR technique). Moreover the generated urea linkage is robust and stable under a variety of conditions including acid, basic, reduction and oxydation steps. A broad range of chemistry is thus allowed in building up the compounds of interest during the production of complex and diverse libraries.

The general usefulness of the new linker is exemplified here by applying it on phenyl rings possessing functional groups such as hydroxy, formyl and amino, which can in turn, after deprotection, be derivatised. A more complex pattern of substitution (e.g. trifluoromethylpiperazine) is amenable as well to the present new linker.

According to the present invention, we provide polymers of general formula (I)

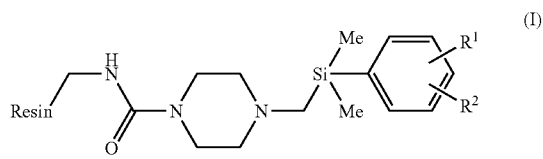

wherein
Resin denotes polystyrene, optionally cross linked with divinyl benzene or polyethylenglycol;
$R^1$ denotes hydrogen, $C_1$–$C_6$-alkyl, $C_2$–$C_6$-alkenyl, $C_2$–$C_6$-alkynyl $C_1$–$C_6$-alkoxy, halogen, $NO_2$ or $CF_3$;
$R^2$ denotes a group selected from hydroxy, amino, preferably N—$C_1$–$C_6$-alkylamino, and formyl, being optionally protected by a suitable protective group, or
  a 5 or 6 membered saturated or unsaturated nitrogen heterocycle, optionally containing one or two additional heteroatoms selected from the group consisting of oxygen, nitrogen and sulfur, and being optionally substituted by a group selected from $C_1$–$C_6$-alkyl, $C_1$–$C_6$-alkoxy, halogen, $NO_2$ and a suitable protective group.

Preferred polymers are those of general formula (I), wherein

Resin denotes polystyrene, optionally cross linked with divinyl benzene or polyethylenglycol;

$R^1$ denotes hydrogen, $C_1$–$C_4$-alkyl, $C_1$–$C_4$-alkoxy, fluorine, chlorine, bromine, or $NO_2$;

$R^2$ denotes a group selected from hydroxy, amino, preferably N—$C_1$–$C_4$-alkylamino, and formyl, being optionally protected by a suitable protective group, or a 5 or 6 membered saturated or unsaturated nitrogen heterocycle, optionally containing one additional nitrogen heteroatom which is substituted by a protective group selected from fluorenylmethyoxycarbonyl and t-butoxycarbonyl.

More preferred polymers are those of general formula (I), wherein

Resin denotes polystyrene cross linked with divinyl benzene;

$R^1$ denotes hydrogen, methyl, methoxy, fluorine, chlorine, bromine, or $NO_2$, preferably hydrogen;

$R^2$ denotes hydroxy, being protected by a group selected from tertbutyldimethylsilyl, methoxy-ethoxymethyl (MEM) and methyl, or N-methylamino, being protected by a group selected from fluorenylmethyloxycarbonyl (FMOC) and t-butoxycarbonyl (BOC), or formyl, being protected to form a dioxolane ring, or piperazin-1-yl, being substituted by a protective group selected from fluorenylmethyoxycarbonyl and t-butoxycarbonyl.

According to the invention the term resin refers to polystyrene, optionally crosss linked with divinyl benzene, preferably with high swelling properties or highly cross linked macroporous polystyrene beads with low swelling capacity or cross linked polystyrene—polyethylenglycol. The preferred one is a resin made with cross linked polystyrene—1% divinylbenzene, 200–400 mesh of the so called Merrifield type.

The alkyl groups meant here (including those which are components of other groups) are branched and unbranched alkyl groups having 1 to 6 carbon atoms, preferably 1 to 4 carbon atoms, such as: methyl, ethyl, n-propyl, iso-propyl, butyl, iso-butyl, sec-butyl, tert-butyl, pentyl, iso-pentyl and hexyl.

Alkenyl groups (including those which are components of other groups) are the branched and unbranched alkenyl groups with 2 to 6 carbon atoms, preferably 2 to 4 carbon atoms, provided that they have at least one double bond, e.g. the alkyl groups mentioned above provided that they have at least one double bond, such as for example vinyl (provided that no unstable enamines or enolethers are formed), propenyl, iso-propenyl, butenyl, pentenyl and hexenyl.

If not otherwise specified the alkenyl- and alkenylen-groups mentioned above are to be understood as embracing optionally existing stereoisomers. Accordingly, for instance the definition 2-butenyl is to be understood as embracing 2-(Z)-butenyl and 2-(E)-butenyl, etc.

The term alkynyl groups (including those which are components of other groups) refers to alkynyl groups having 2 to 6, preferably 2 to 4 carbon atoms provided that they have at least one triple bond, e.g. ethynyl, propargyl, butynyl, pentynyl and hexynyl.

The term amino denotes a group selected from $NH_2$, N—$C_1$–$C_6$-alkylamino, preferably N—$C_1$–$C_4$-alkylamino, N-di($C_1$–$C_6$-alkyl)amino, preferably N-di($C_1$–$C_4$-alkyl)amino, wherein $C_1$–$C_6$-alkyl is as hereinbefore defined. Preferred amino groups are selected from N-methylamino and N-ethylamino, preferably N-methylamino.

The suitable protective groups that are applicable according to the invention may differ depending on the functional group they protect. For the hydroxy group the suitable protective group is preferably selected from methoxymethyl, benzyloxymethyl, t-butoxymethyl, tertbutyldimethylsilyl, tetrahydropyranyl, methoxyethoxyethyl and benzyl, preferred protecting group being tertbutyldimethylsilyl. For the amino group the suitable protective group is preferably selected from fluorenylmethyloxycarbonyl (FMOC), benzyloxycarbonyl, t-butoxycarbonyl (BOC), allyloxycarbonyl preferred protecting group being FMOC and BOC. The formyl group is preferably protected by a protective group to form a group selected from 1,3-dioxolane, 1,3-dithiolane, preferred protecting group being 1,3-dioxolane.

If not otherwise specified preferred examples of 5- or 6-membered nitrogen heterocycles are as follows: piperazine, pyrrolidine, piperidine, morpholine, benzimidazole, benzoxazole, imidazole, pyrazole, preferably piperazine, morpholine, piperidine.

Halogen, stands for fluorine, chlorine, bromine or iodine, preferably chlorine or bromine.

"=O" means an oxygen atom linked by a double bond.

The compounds of general formula (I) may be conveniently prepared following the method described in scheme 1.

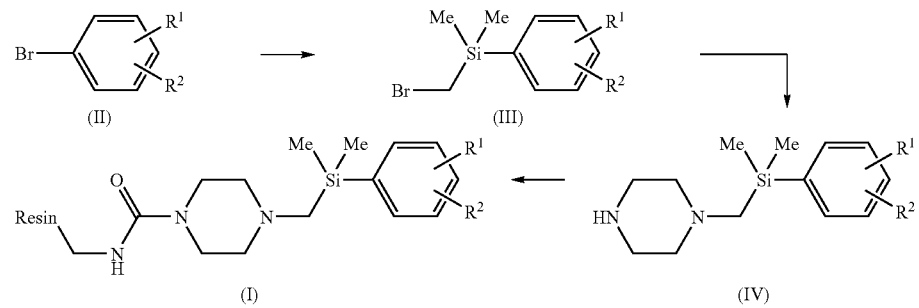

Scheme 1:

groups with 2 to 6 carbon atoms, preferably 2 to 4 carbon atoms, provided that they have at least one double bond, e.g.

The bromo-derivatives of formula (II) are obtainable via conventional methods known in the art. Those derivatives of formula (II) wherein $R^2$ denotes a functional group being protected as hereinbefore defined are obtainable from the unprotected starting materials according to well known methods in the art, pertaining to the introduction of known protective groups. Starting from the appropriate bromoderivatives of formula (II) the silyl-derivatives of formula (III) are available as follows. After activation by suitable organometallic reagents, preferably lithium alkyl reagents, more preferably branched or unbranched butyllithium reagents, at low temperature, preferably between −78° C. and −20° C., most preferably between −40° C. and −60° C., in an appropriate organic solvent, preferably in a solvent selected from the group consisting of tetrahydrofurane and diethylether, the dimethyl silyl bromomethyl chain is introduced to by addition of the appropriate chlorosilane to generate compound of formula (III). To obtain the compounds of formula (IV) on the compounds of formula (III) a piperazine spacer is added by reaction with excess piperazine or using a Fmoc or Boc monoprotected piperazine in the presence of a base selected from the group triethylamine, pyridine, diisopropylethylamine, with diisopropylethylamine being the most preferred base to catch the generated acid. The reaction is preferably conducted under heating, preferably between 40–120° C., more preferred between 60–100° C. in an organic solvent selected from the group consisting of dimethylsulfoxide, N-methyl-pyrrolidone (NMP), ethanol wherein dimethylsulfoxide is most preferred. The compounds of formula (I) are obtained by reacting a slight excess (1.5 equivalent) of the compounds of formula (IV) with a polymeric resin being functionalized by isocyanate-groups. The reaction is preferably conducted in an apolar solvent selected from the group consisting of tetrahydrofurane, DMF, dichloromethane, with tetrahydrofurane being the most preferred solvent at moderate temperatures (between 0–40° C., preferably between 20–30° C.). Optionally the addition of a base, preferably of an organic base selected from the amines mentioned hereinbefore may be advisable. The most preferred base is disiopropylethylamine.

As apparent from scheme 1 the intermediate products of formula (IV) are key intermediates for the synthesis of the compounds of formula (I). Therfore, a further aspect of the invention relates to intermediate compounds of formula (IV)

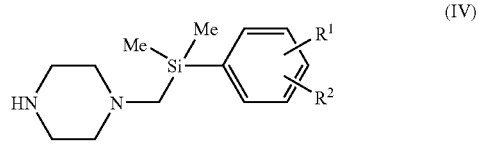

(IV)

wherein
$R^1$ denotes hydrogen, $C_1$–$C_6$-alkyl, $C_2$–$C_6$-alkenyl, $C_2$–$C_6$-alkynyl $C_1$–$C_6$-alkoxy, halogen, $NO_2$ or $CF_3$;
$R^2$ denotes a group selected from hydroxy, amino, preferably N—$C_1$–$C_6$-alkylamino, and formyl, being optionally protected by a suitable protective group, or
a 5 or 6 membered saturated or unsaturated nitrogen heterocycle, optionally containing one or two additional heteroatoms selected from the group consisting of oxygen, nitrogen and sulfur, and being optionally substituted by a group selected from $C_1$–$C_6$-alkyl, $C_1$–$C_6$-alkoxy, halogen, $NO_2$ and a suitable protective group.

Preferred intermediates are those of general formula (IV), wherein
$R^1$ denotes hydrogen, $C_1$–$C_4$-alkyl, $C_1$–$C_4$-alkoxy, fluorine, chlorine, bromine, or $NO_2$;
$R^2$ denotes a group selected from hydroxy, amino, preferably N—$C_1$–$C_4$-alkylamino, and formyl, being optionally protected by a suitable protective group, or
a 5 or 6 membered saturated or unsaturated nitrogen heterocycle, optionally containing one additional nitrogen heteroatom which is substituted by a protective group selected from fluorenylmethyoxycarbonyl and t-butoxycarbonyl.

More preferred intermediates are those of general formula (IV),
wherein
$R^1$ denotes hydrogen, methyl, methoxy, fluorine, chlorine, bromine, or $NO_2$, preferably hydrogen;
$R^2$ denotes hydroxy, being protected by a group selected from tertbutyldimethylsilyl, methoxy-ethoxymethyl (MEM) and methyl, or
N-methylamino, being protected by a group selected from fluorenylmethyloxycarbonyl (FMOC) and t-butoxycarbonyl (BOC), or
formyl, being protected to form a dioxolane ring, or
piperazin-1-yl, being substituted by a protective group selected from fluorenylmethyoxycarbonyl and t-butoxycarbonyl.

The compounds of formula (I) wherein $R^2$ denotes a suitably protected hydroxy, amino or formyl group can be deprotected via conventional methods. The methods for the cleavage of the protective groups being applicable according to the invention are well known in the art. After cleavage of the protective group the hydroxy, amino or formyl group can be further derivatised via conventional methods to lead to compounds of formula (I')

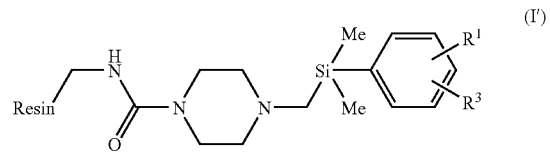

(I')

wherein
Resin and $R^1$ are as hereinbefore defined and
$R^3$ denotes a group selected from —O—CO—$C_1$–$C_4$-alkyl, —N($C_1$–$C_4$-alykl)$_2$, —NH—CO—$C_1$–$C_4$-alkyl, —NH—CO—O$C_1$–$C_4$-alkyl, —NH—CO—NH—$C_1$–$C_4$-alkyl, —COOH, —COO$C_1$–$C_4$-alkyl and —CONH$C_1$–$C_4$-alkyl and —$CH_2OH$.

Compounds of formula (I') wherein $R^3$ denotes —O—CO—$C_1$–$C_4$-alkyl are obtainable via conventional ester syntheses either under acid or basic reaction conditions starting from compounds of formula (I) wherein $R^2$ denotes hydroxy. Compounds of formula (I') wherein $R^3$ denotes —N($C_1$–$C_4$-alykl)$_2$ are obtainable from the compounds of formula (I) wherein $R^2$ denotes $NH_2$ or —NH$C_1$–$C_4$-alkyl via conventional methods by treatment with $C_1$–$C_4$-alkylhalides, -triflates, -mesylates or -p-toluenesulfonates under basic reaction conditions. Compounds of formula (I') wherein $R^3$ denotes —NH—CO—$C_1$–$C_4$-alkyl are obtainable from the compounds of formula (I) wherein $R^2$ denotes $NH_2$ via conventional methods by treatment with $C_1$–$C_4$- alkyl-carboxylic acid esters, anhydrides or acyl halydes under basic reaction conditions. Compounds of formula (I') wherein $R^3$ denotes —NH—CO—$OC_1$–$C_4$-alykl are obtainable from the compounds of formula (I) wherein $R^2$ denotes $NH_2$ via conventional methods by treatment with $C_1$–$C_4$-alkyl-chloroformates under basic reaction conditions. Compounds of formula (I') wherein $R^3$ denotes —NH—CO—NH—$C_1$–$C_4$-alkyl are obtainable via conventional methods by treatment with —$C_1$–$C_4$-alkyl-isocyanates. Compounds of formula (I') wherein $R^3$ denotes —COOH are obtainable from the compounds of formula (I) wherein $R^2$ denotes formyl via conventional oxidation methods. Compounds of formula (I') wherein $R^3$ denotes —CO—$OC_1$–$C_4$-alkyl are obtainable via conventional ester syntheses either under acid or basic reaction conditions starting from compounds of formula (I') wherein $R^3$ denotes —COOH. Compounds of formula (I') wherein $R^3$ denotes —$CONHC_1$–$C_4$-alkyl are obtainable from the compounds of formula (I') wherein $R^3$ denotes —CO—$OC_1$–$C_4$-alkyl via conventional methods by treatment with amines of formula —$NHC_1$–$C_4$-alkyl under basic reaction conditions. Compounds of formula (I') wherein $R^3$ denotes —$CH_2OH$ are obtainable from the compounds of formula (I) wherein $R^2$ denotes formyl via conventional reductive methods.

The compounds of formula (I) (or (I')) can be easily cleaved from the resin under mild reaction conditions to lead to the products of formula (V) (scheme 2).

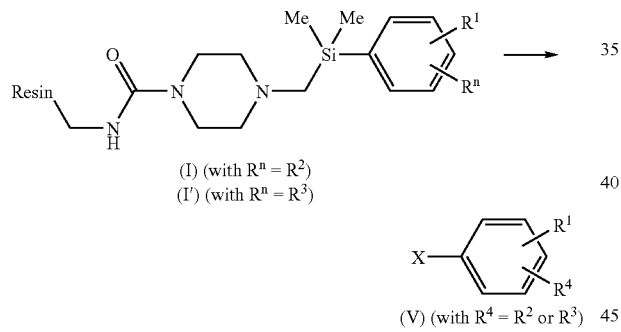

Scheme 2:

Depending on the reaction conditions for the cleavage step according to scheme 2 X may either denote hydrogen, halogens (Br, F, I) or —COMe.

Compounds (V) wherein X denotes hydrogen are obtainable by reacting compounds of formula (I) or (I') with tetrabutylammonium fluoride (TBAF), Cesium fluoride, KF, trifluoroacetic acid or triflic acid, preferably with TBAF under the reaction conditions that are usually applied for analogous cleavage reactions known in the art.

Compounds (V) wherein X denotes bromine are obtainable by reacting compounds of formula (I) or (I') with N-bromo succinimide (NBS) or $Br_2$, preferably with NBS under the reaction conditions that are usually applied for analogous cleavage reactions known in the art. Compounds (V) wherein X denotes fluorine are obtainable by reacting compounds of formula (I) or (I') with $BF_3$ under the reaction conditions that are usually applied for analogous cleavage reactions known in the art. Compounds (V) wherein X denotes iodine are obtainable by reacting compounds of formula (I) or (I') with I—Cl under the reaction conditions that are usually applied for analogous cleavage reactions known in the art. Compounds (V) wherein X denotes —COMe are obtainable by reacting compounds of formula (I) or (I') with acethyl chloride in the presence of $AlCl_3$ under the reaction conditions that are usually applied for analogous cleavage reactions known in the art.

The following examples illustrate the preparation of all the new compounds included in the present invention. It should be understood that the invention is not limited to the given examples of chemical methods and processes for the preparation of the substances, as other conventional methods well known to those skilled in the art, are suitable too.

DESCRIPTION 1

1-(3-Bromo-5-trifluoromethyl-phenyl)-piperazine

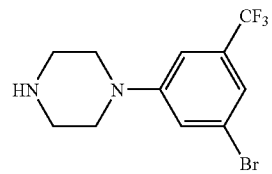

A solution of 1-bromo-3-fluoro-5-(trifluoromethyl)-benzene (100 g, 0.41 moles), piperazine (194.9 g, 2.26 moles) in DMSO (800 ml) was heated at 100° C. for 5 hours, cooled at room temperature and stirred overnight. The mixture was poured into water and the yellow solid which separeted was filtered. The solid was suspended in a 5% THF solution in water (300 ml) water/THF, stirred for 1 hour and filtered again.

120 g, light beige solid, m.p. 74–77° C.

DESCRIPTION 2 tert-Butyl-4-[3-bromo-5-(trifluoromethyl)-phenyl]-1-piperazine carboxylate

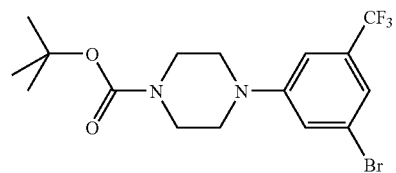

A solution of 1-(3-bromo-5-trifluoromethyl-phenyl)-piperazine (115 g, 0.37 moles) in THF (550 ml) was added dropwise to a solution of di-tert-butyl dicarbonate (81.2 g, 0.37 moles) in THF (250 ml) at 20° C. The reaction mixture was stirred overnight at room temperature. The reaction mixture was taken to dryness and from the residue, after crystallisation from water/THF, the title compound was obtained.

151 g, beige solid, m.p 100–103° C.

According to the above described procedure, the following compounds were prepared:

tert-Butyl 3-bromophenyl-carbamate

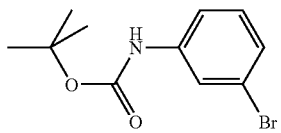

6.7 g, yellowish solid, m.p. 88–91° C.

DESCRIPTION 3

(3-Bromophenoxy)-(tert-butyl)-dimethylsilane

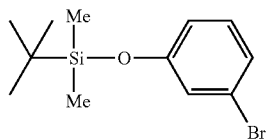

A suspension of 3-bromo-phenol (5.5 g, 31.8 mmoles), imidazole (4.3 g, 63.6 mmoles) in $CH_2Cl_2$ (70 ml) was added dropwise to a solution of tert-butyl-chloro-dimethyl-silane (5.3 g, 35 mmoles) in $CH_2Cl_2$ (5 ml) at 0° C. The reaction mixture was stirred for 3 hours at room temperature then evaporated to dryness under vacuum. The residue was partitioned between water and ethyl acetate and from the organic solution after essiccation over $MgSO_4$, filtration and evaporation the title compound was obtained.

7.5 g, yellow oil $^1$H-NMR (CDCl$_3$; 200 MHz) 7.05–7.11 (ov, 2H); 7.00 (m, 1H); 6.76 (m, 1H); 0.97 (s, 9H): 0.20 (s, 6H)

DESCRIPTION 4

Tert-butyl-3-bromophenyl-N-methyl carbamate

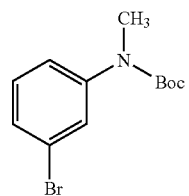

A solution of tertbutyl-3-bromo-phenyl-carbamate (14 g, 51.4 mmoles) in DMF (90 ml) were added dropwise to a suspension of 80% NaH (1.85 g, 61.7 mmoles) in DMF (30 ml) al 10° C. The reaction mixture was stirred for 1 h at room temperature then a solution of CH$_3$I (6.4 ml, 102.88 mmoles) in DMF (30 ml) was added dropwise at 1020 C. The reaction mixture was stirred overnight at room temperature then evaporated to dryness under vacuum. The residue was partitioned between water and diethyl-ether and the title compound was obtained by evaporating organic layer.

14.28 g; yellow oil.

$^1$H-NMR (CDCl$_3$; 200 MHz) 7.43 (m, 1H); 7.34 (m, 1H); 3.61 (m, 4H); 7.1–7.2 (ov, 2H); 3.25 (s, 3H); 1.46 (s, 9H)

DESCRIPTION 5 tert-Butyl-4-[3-[(bromomethyl)-(dimethyl)silyl]-5-(trifluoromethyl)-phenyl]-1-piperazine carboxylate

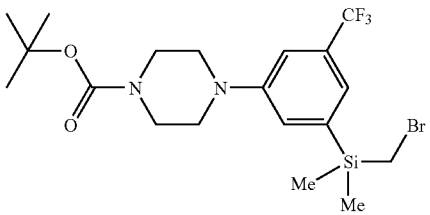

A solution of tert-butyl 4-[3-bromo-5-(trifluoromethyl)-phenyl]-1-piperazine carboxylate (75 g, 183 mmoles) in diethyl ether, previously dried on molecular sieves, (1000 ml) was cooled to −65° C. and a 1.7M solution of tert-butyl lithium (215.6 ml, 366 mmoles) was added. After 30 minutes stirring bromomethyl-dimethyl-chlorosilane (49.9 ml, 366 mmoles) was added dropwise. After 2 hours stirring at −65° C., the reaction mixture was left at room temperature overnight. Water (600 ml) was added and the organic layer was washed with water, dried on $MgSO_4$, filtered and evaporated.

114 g, yellowish oil $^1$H-NMR (CDCl$_3$; 200 MHz) 7.2–7.3 (ov, 2H); 7.13 (b, 1H); 3.61 (m, 4H); 3.19 (m, 4H); 2.63 (s, 2H); 1.49 (s, 9H); 0.45 (s, 6H)

According to the above described procedure, the following compounds were prepared:

Bromomethyl-[3-(1,3-dioxolan-2-yl)-phenyl]-dimethylsilane

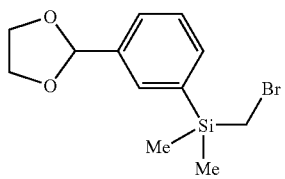

The crude compound was purified by flash chromatography (Silica-gel, eluent n-hexane-ethyl acetate 90-10).

5.7 g yellowish oil

MS (APCl+) [M+H]$^+$=302

The compound was pure enough to be used in the following step, without further characterization.

Bromomethyl-(3-{[tert-butyl-(dimethyl)-silyl]-oxy}-phenyl)-dimethylsilane

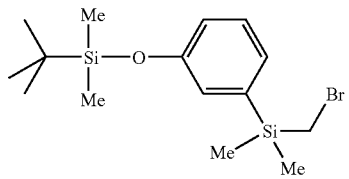

The crude compound was purified by flash chromatography (Silica-gel, eluent n-hexane-ethyl acetate 97-3).
700 mg, yellow oil
¹H-NMR (CDCl₃; 200 MHz) 7.25 (m, 1H); 7.10 (m, 1H); 7.00 (m, 1H); 6.86 (m, 1H); 2.61 (s, 2H); 0.99 (s, 9H); 0.41 (s, 6H); 0.20 (s, 6H)

tert-Butyl-3-[(bromomethyl)-(dimethylsilyl)]-phenyl]-N-methyl carbamate

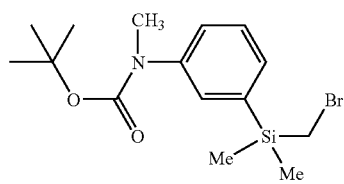

The crude compound was purified by flash chromatography (silica-gel; eluent hexane-ethyl acetate 98:2). 12.1 g.
MS (APCl+) [M+H]⁺=359

DESCRIPTION 6 tert-Butyl-4-[3-[dimethyl-(1-piperazinylmethyl)-silyl]-5-(trifluoromethyl)-phenyl]-1-piperazine carboxylate

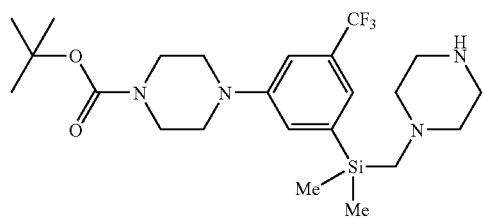

A solution of tert-butyl 4-[3-[(bromomethyl)-dimethylsilyl]-5-(trifluoromethyl)-phenyl]-1-piperazine carboxylate (114.7 g, 0.24 moles) piperazine (205.2 g, 2.38 moles) and DIPEA (203.7 ml, 1.19 moles) in DMSO (1000 ml) was heated to 80° C. for 6 hours, cooled to room temperature and stirred overnight. The reaction was poured in water (6 l) and the separated orange oil was extracted into ethyl acetate. The organic layer was washed with a saturated NaCl water solution, dried on MgSO₄, filtered and evaporated. From the oily residue, after a flash chromatography purification (Silica-gel, eluent CH₂Cl₂—MetOH—NH₄OH 90-10-1) the pure title compound was obtained.

24 g, ivory solid, m.p. 179–180° C.
¹H-NMR: (CDCl₃; 200 MHz) 7.2–7.4 (ov, 2H); 7.09 (b, 1H); 3.61 (m, 4H); 3.19 (m, 4H); 2.84 (m, 4H); 2.35 (m, 4H); 2.14 (s, 2H); 1.93 (b, 1H+HDO); 1.49 (s, 9H); 0.34 (s, 6H)

According to the above described procedure, the following compounds were prepared:

1-{[[3-(1,3-Dioxolan-2-yl)-phenyl]-dimethylsilyl]-methyl}-piperazine

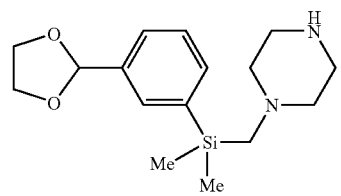

The compound was obtained after traditional work-up (acid and basic extraction) with a purity good enough to be used without any further purification.
1.4 g, thick oil
MS (APCl+) [M+H]⁺=307

1-{[(3-{[tert-Butyl-dimethylsilyl]-oxy}-phenyl)-dimethylsilyl]-methyl}-piperazine

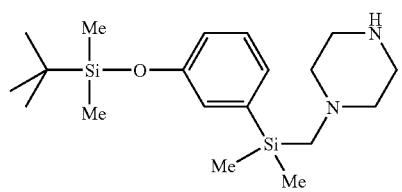

230 mg yellowish oil
¹H-NMR (CDCl₃; 200 MHz) 7.22 (m, 1H); 7.10 (m, 1H); 7.00 (m, 1H); 6.83 (m, 1H); 3.52 (b, 1H+HDO); 2.95 (m, 4H); 2.46 (m, 4H); 2.15 (s, 2H); 0.99 (s, 9H); 0.31 (s, 6H); 0.19 (s, 6H)

tert-Butyl-3-[dimethyl-(1-piperazinylmethyl)-silyl]-phenyl] N-methyl carbamate

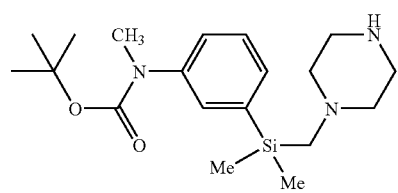

6.8 g; yellow oil

¹H-NMR (CDCl₃; 200 MHz) 7.2–7.4 (ov, 4H); 4.1 (b, 1H); 3.26 (s, 3H); 3.00 (m, 4H); 2.51 (m, 4H); 2.18 (s, 2H); 1.44 (s, 9H); 0.33 (s, 6H)

DESCRIPTION 7

Piperazin, 1-carbamylmethyl-polistyren resin-4-{[3-trifluoromethyl-5-(4-t-butoxycarbonylpiperazin-1-yl)]-phenyl}-dimethylsilylmethyl

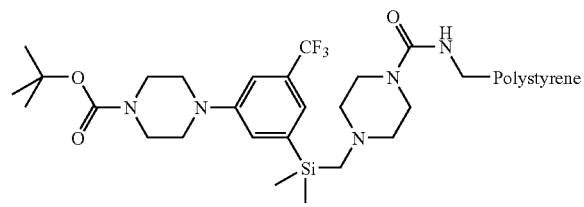

A solution of tert-butyl 4-[3-[dimethyl-(1-piperazinylmethyl)-silyl]-5-(trifluoromethyl)-phenyl]-1-piperazine carboxylate (15.2 g, 31.2 mmoles), DIPEA (5.35 ml, 31.2 mmoles) in THF (250 ml) was added to (isocyanate)-polystyrene resin (11.5 g, 20.8 mmoles, loading 1.91 mmol/g) and left at room temperature overnight under gently stirring. The resin was rinsed with THF (×5 ml), DMF (×5 ml), THF (×5 ml) and CH₂Cl₂ (×5 ml) and then dried under vacuum at room temperature.

18.4 g orange resin

¹H-NMR (solid state; gel phase in CD₂Cl₂; 300 MHz) 3.51 (4H); 3.24 (4H); 3.12 (4H); 2.29 (4H); 2.12 (2H); 1.41 (9H); 0.30 (6H)

According to the above described procedure, the following compounds were prepared:

Piperazin, 1-carbamylmethyl-polistyren resin-4-[3-(1,3-Dioxolan-2-yl)-phenyl]-dimethylsilylmethyl

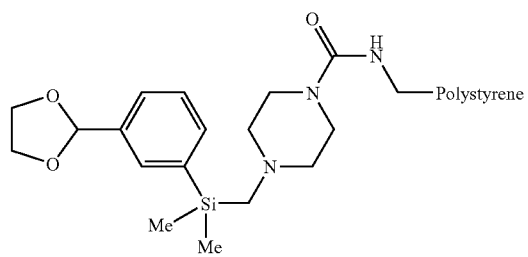

The resin bound compound was obtained starting from 150 mg of (isocyanate)-polystyrene resin.

150 mg, yellowish resin

¹H-NMR (solid state; gel phase in CD₂Cl₂; 300 MHz) 5.72 (1H); 3.9–4.1 (4h); 3.26 (4H); 2.31 (4H); 2.16 (2H); 0.37 (6H)

Piperazin, 1-carbamylmethyl-polistyren resin-4-[3-(tert-Butyl-dimethylsilyl-oxy)-phenyl]-methyl-dimethylsilyl

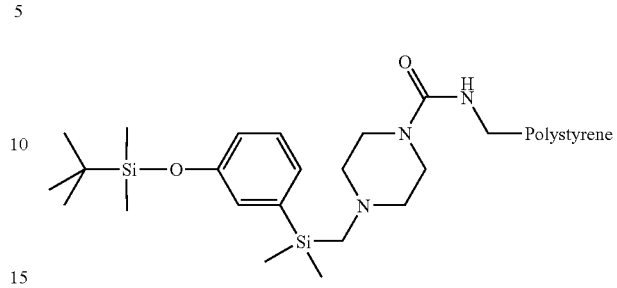

The resin bound compound was obtained starting from 300 mg of (isocyanate)-polystyrene resin.

300 mg, resin

¹H-NMR (solid state; gel phase in CD₂Cl₂; 300 MHz) 3.24 (4H); 2.29 (4H); 2.11 (2H); 0.96 (9H); 0.29 (6H); 0.17 (6H)

Piperazin, 1-carbamylmethyl-polistyren resin-4-{[3-(N-methyl-N-tert-butoxycarbonyl)-amino]}-methyl-dimethylsilylphenyl

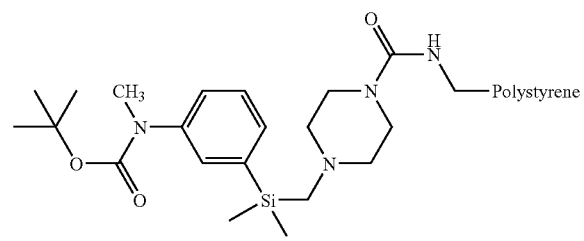

The resin bound compound was obtained starting from 1 g of (isocyanate)-polystyrene resin.

1 g, resin

¹H-NMR (solid state; gel phase in CD₂Cl₂; 300 MHz) 3.2 (4H); 3.19 (3H); 2.30 (4H); 2.13 (2H); 1.41 (9H); 0.32 (6H)

DESCRIPTION 8

Piperazin, 1-carbamylmethyl-polistyren resin-4-{[3-trifluoromethyl-5-(piperazin-1-yl)]-phenyl}-methyl-dimethylsilyl

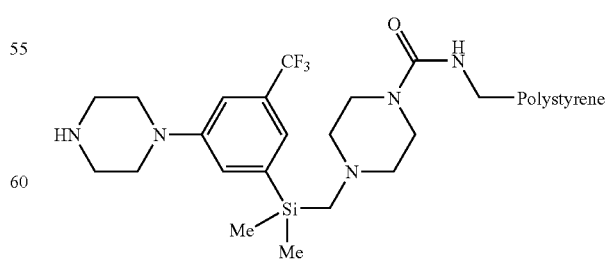

Piperazin, 1-carbamylmethyl-polistyren resin-4-{[3-trifluoromethyl-5-(4-t-butoxycarbonylpiperazin-1-yl)]-phenyl}-methyl-dimethylsilyl (14 g, 13.9 mmoles) was added to a 30% TFA solution in CH$_2$Cl$_2$ (200 ml). The slurry was gently stirred for 1.5 hour at room temperature, filtered and the resin was added to a 30% DBU solution in CH$_2$Cl$_2$ and the slurry was stirred for 1 hour at room temperature. The solvent was removed by filtration and the resin was rinsed with CH$_2$Cl$_2$, MetOH and CH$_2$Cl$_2$ and then dried under vacuum.

14 g yellowish resin
$^1$H-NMR (solid state; gel phase in CD$_2$Cl$_2$; 300 MHz) 3.18 (8H); 3.00 (4H); 2.30 (4H); 2.13 (2H); 0.31 (6H)

DESCRIPTION 9

Piperazin, 1-carbamylmethyl-polistyren resin-4-[3-(Formyl)-phenyl]-methyl-dimethylsilyl

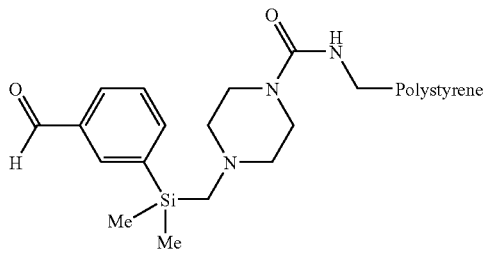

Piperazin, 1-carbamylmethyl-polistyren resin-4-[3-(1,3-Dioxolan-2-yl)-phenyl]-methyl-dimethylsilyl (130 mg) was added to a 5% solution of HCl in THF. The slurry was gently stirred at room temperature overnigth, filtered and the resin was rinsed with THF, CH$_2$Cl$_2$, 5% DIPEA, MetOH and CH$_2$Cl$_2$.

120 mg, yellowish resin
$^1$H-NMR (solid state; gel phase in CD$_2$Cl$_2$; 300 MHZ) 9.97 (1H); 3.27 (4H); 2.31 (4H); 2.17 (2H); 0.38 (6H)

DESCRIPTION 10

Piperazin, 1-carbamylmethyl-polistyren resin-4-[3-(hydroxy)-phenyl]-methyl-dimethylsilyl

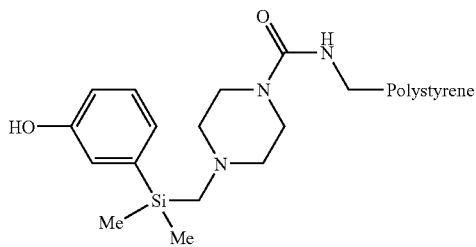

Piperazin, 1-carbamylmethyl-polistyren resin-4-[3-(tert-Butyl-dimethylsilyl-oxy)-phenyl]-methyl-dimethylsilyl (230 mg) was added to a 5% solution of TFA in CH$_2$Cl$_2$ and the suspension was gently stirred for 1 hour at room temperature. The slurry was rinsed with CH$_2$Cl$_2$, 5% DIPEA in CH$_2$Cl$_2$ (×5), MetOH (×5) and CH$_2$Cl$_2$ (×5).

200 mg yellowish resin
$^1$H-NMR (solid state; gel phase in CD$_2$Cl$_2$; 300 MHz) significative features: disappareance of peak at 0.96 ppm (9H); peak at 2.26 ppm (6H)

According to the above described procedure, using 20% solution of TFA in CH$_2$Cl$_2$ the following compound was prepared:

Piperazin, 1-carbamylmethyl-polistyren resin-4-{[3-(N-methylamino]}-methyl-dimethylsilylphenyl

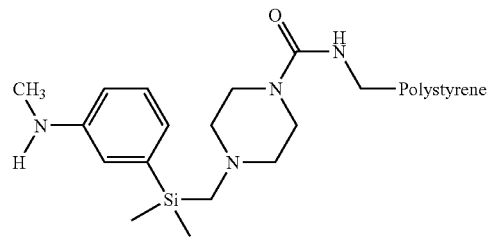

100 mg resin
$^1$H-NMR (solid state; gel phase in CD$_2$Cl$_2$; 300 MHz): 3.22 (b, 4H); 2.69 (b, 3H); 2.28 (b, 4H); 2.09 (b, 2H); 0.27 (b, 6H)

DESCRIPTION 11

1-[3-(Trifluoromethyl)-phenyl]-piperazine

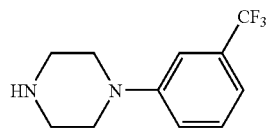

Piperazin, 1-carbamylmethyl-polistyren resin-4-{[3-trifluoromethyl-5-(piperazin-1-yl)]-phenyl}-methyl-dimethylsilyl (50 mg, 0.035 mmoles) was added to a solution of tetrabutyl ammonium fluoride (22 mg, 0.07 mmoles) in DMF (1 ml). The slurry was heated to 60° C. under stirring for 5 hours and filtered. To this solution Amberlyst 15 resin (100 mg) and a calcium sulfonate resin (100 mg) were added and the mixture was stirred for 8 hours at room temperature. After filtration, the solution was evaporated to dryness into a speed-vac apparatus to give the title compound 3.5 mg, oily
$^1$H-NMR (CDCl3; 200 MHz) 7.34 (m, 1H); 7.0–7.2 (ov, 2H); 3.16 (m, 4H); 3.05 (m, 4H); 1.66 (b, 1H)

According to the above described procedure, the following compounds were prepared:

Benzaldehyde

The title compound was obtained starting from 140 mg of Piperazin, 1-carbamylmethyl-polistyren resin-4-[3-(Formyl)-phenyl]-methy-dimethylsilyll 4.5 mg yellowish oil The identity of the product was confirmed by GC-MS in comparison to an authentical commercial sample.

Phenol

The title compound was obtained starting from 140 mg of Piperazin, 1-carbamylmethyl-polistyren resin-4-[3-(hydroxy)-phenyl]-methyl-dimethylsilyl 3.8 mg yellowish oil The identity of the product was confirmed by GC-MS in comparison to an authentical commercial sample.

N-Methyl-aniline

The title compound was obtained starting from 140 mg of Piperazin, 1-carbamylmethyl-polistyren resin-4-{[3-(N-methylamino]}-methyl-dimethylsilylphenyl 4.2 mg yellowish oil.

What is claimed is:

1. A compound of formula (IV)

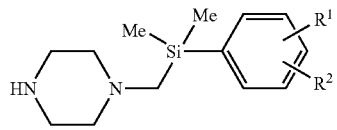

wherein

R¹ denotes hydrogen, $C_1$–$C_6$-alkyl, $C_2$–$C_6$-alkenyl, $C_2$–$C_6$-alkynyl $C_1$–$C_6$-alkoxy, halogen, $NO_2$ or $CF_3$; and R² denotes a group selected from hydroxy, amino, and formyl, being optionally protected by a suitable protective group.

2. The compound as recited in claim 1 wherein R² is N—$C_1$–$C_6$-alkylamino, optionally protected by a suitable protective group.

* * * * *